United States Patent [19]

Withers et al.

[11] Patent Number: 4,524,776
[45] Date of Patent: Jun. 25, 1985

[54] SPLIT CARRIER FOR EYELID SENSOR AND THE LIKE

[76] Inventors: Stanley J. Withers, 4701 San Leandro St., Oakland, Calif. 94601; Gary E. Schneiderman, 640 Mandarin La., Walnut Creek, Calif. 94598; William M. Little, Jr., 1059 Norwood Ave., Oakland, Calif. 94610

[21] Appl. No.: 545,908

[22] Filed: Oct. 27, 1983

[51] Int. Cl.³ ............................................... A61B 5/04
[52] U.S. Cl. .................................. 128/644; 128/652; 604/893
[58] Field of Search ........ 128/635, 652, 639, 644–647, 128/676; 604/893, 294

[56] References Cited

U.S. PATENT DOCUMENTS

| | | | |
|---|---|---|---|
| 3,067,749 | 12/1962 | Walters | 128/644 X |
| 3,323,516 | 6/1967 | Salter | 128/644 |
| 3,769,961 | 11/1973 | Fntt et al. | 128/635 |
| 3,995,635 | 12/1976 | Higuchi et al. | 604/893 |
| 4,089,329 | 5/1978 | Couvillon et al. | 128/652 |

Primary Examiner—Edward M. Coven
Attorney, Agent, or Firm—Flehr, Hohbach, Test, Albritton & Herbert

[57] ABSTRACT

For use with the human eye, especially, there is provided a relatively narrow, split, flexible partial ring adapted to fit against the portion of the eyeball behind the upper and lower eyelids. The corneal opening is of an extent so that despite normal excursions of the cornea, the cornea does not substantially contact the ring. The split ring is formed of highly flexible material so as to permit a substantially universal fit and at the same time exert minimal effect on the physiological parameters being measured. A sensor or other device is located on a widened portion of the carrier in contact with the palpebral conjunctiva. A conductor or other transmission device may lead from the device through a projection, preferably integral with the ring, and extending beyond the eyelids. The device carrier is a split ring and relies upon its shape and self-resiliency in order to maintain its position within the eye.

13 Claims, 8 Drawing Figures

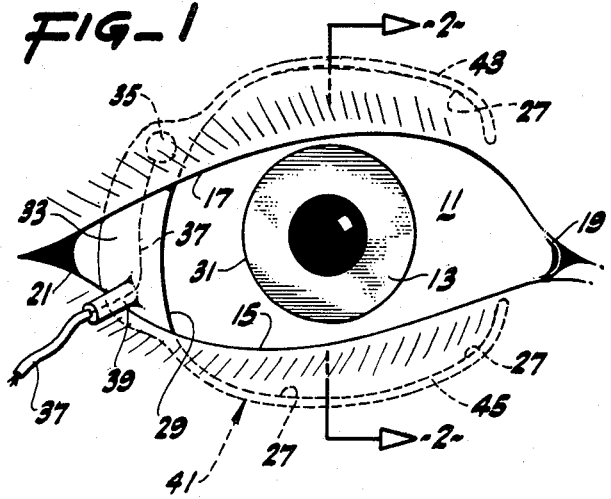
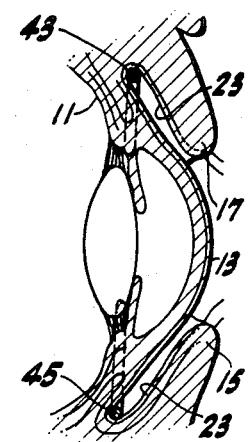
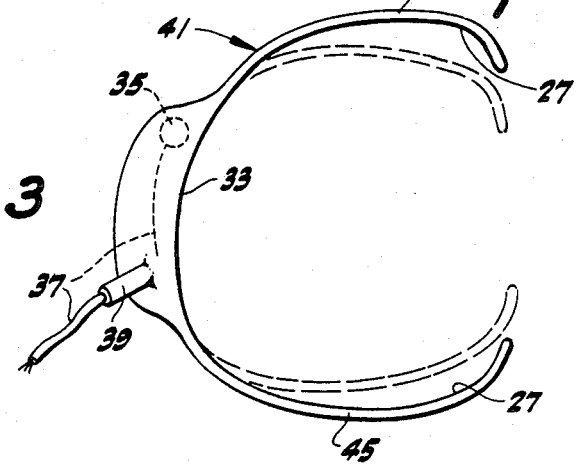
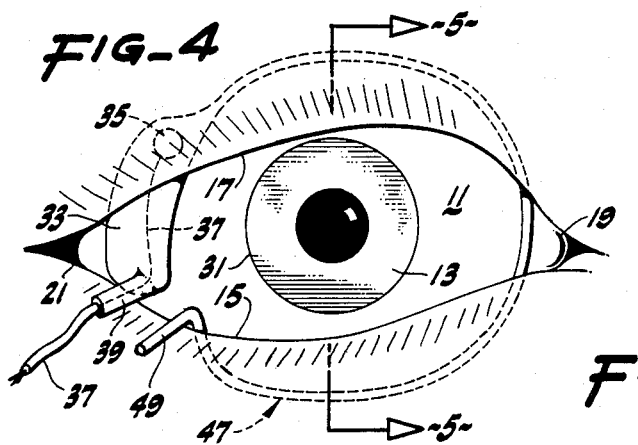
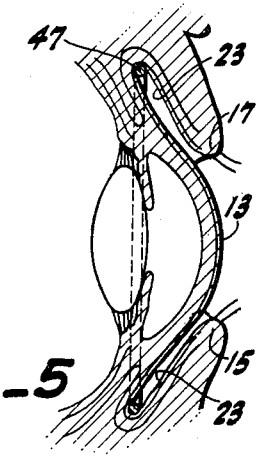

SPLIT CARRIER FOR EYELID SENSOR AND THE LIKE

Carriers for eyelid sensors and the like have been developed in the past. All of these carriers have been fully closed rings which are received between the sclera of the eyeball and the eyelids and provide a support for various sensors in contact with the conjunctival tissue of the eye. Two such carriers and sensors are shown in U.S. Pat. Nos. 3,769,961 and 4,089,329 and there is further disclosure in U.S. Pat. No. Re. 29,703. Moreover, such a carrier is at least partially disclosed in copending patent application Ser. No. 255,682 filed Apr. 20, 1981 for Combination Membraning Tool, Package and Calibration Unit for Eyelid Sensor or the Like. As described, sensors disposed in such carriers have been very valuable in the detection of various factors in the human or animal body in that they establish a detecting mechanism in contact with the palpebral conjunctiva on the inner surface of the eyelid, usually the upper eyelid. The carriers, of course, are useful not only to emplace sensors against the conjunctival surface but also to position other devices against the conjunctiva or the sclera. Such other devices, may, for instance, include medication dispensers. While the eyelid device carriers of the prior art, particularly those set forth in the art cited above, have been successful there are, of course, some limitations and these are met at least in part by the invention set forth herein.

One of the difficulties of the prior art eyelid carriers is that since the closed ring of the carrier is of fixed configuration, it must be sized to some extent to fit the particular user. For instance, eyelid sensor carriers such as disclosed in the aforementioned application Ser. No. 255,682 are such that a single size fits about 70% of the adult population but the quality of the fit to that 70% may vary somewhat. While 70% is a substantial part of the population it is clear that a more universal and better quality fit would be highly beneficial. Moreover, the carrier as shown generally in said patent application may, in some individuals, have a tendency to shift position beneath the eyelids. Further, on the carriers of the prior art, the sensor is universally located on the temporal side. While this location is desirable in many instances, location on the nasal side may provide certain benefits not previously recognized.

Moreover, because of the fixed configuration and size of the above mentioned prior art fully-closed ring carriers, the carriers may, themselves, by their physical presence often have a tendency to substantially alter the various physiological parameters which are to be measured by the incorporated sensor so that accurate readings may not be obtained.

It is, therefore, a general object of the present invention to provide an improved eyelid device carrier providing a more universal and better quality fit.

It is another object of the present invention to provide an improved eyelid device carrier which is more easily and safely inserted into its location under the eyelids.

It is another object of the present invention to provide an improved eyelid device carrier having a greater ability to maintain its position in the eye compared with those of the prior art.

It is another object of the present invention to provide an improved eyelid device carrier wherein the carrier itself creates a minimal obstruction in the conjunctival sac, so as to minimize interference with the physiological parameters being measured.

In accordance with the above objects, an eyelid device carrier supports one or more sensors or other devices against the user's palpebral conjunctiva (upper or lower eyelid) or, against the sclera. The carrier includes a thin flexible split (i.e. partial) ring which is received between the sclera of the eyeball and the eyelids and defines a central opening sufficiently large to allow substantial movement of the eyeball with minimal contact between the cornea and the ring. A device is located in the ring with a portion exposed for contact with the palpebral conjunctiva, the sclera, or both the sclera and the palpebral conjunctiva. The ring itself is formed of a material which is sufficiently flexible and thin that in combination with its split nature, the ring provides little or no interference with the physiological parameters of the palpebral conjunctiva.

FIG. 1 is an elevational view of an eyelid device split ring carrier in accordance with one embodiment of the invention as shown in position in the wearer's eye.

FIG. 2 is a cross section, the plane of which is indicated by the line 2—2 of FIG. 1.

FIG. 3 is an elevational view of the eyelid device carrier shown in FIGS. 1 and 2 with the carrier shown in full lines in its free position and in dashed lines generally in the position it assumes while in the wearer's eye.

FIG. 4 is an elevational view of an eyelid device carrier in accordance with another embodiment of the invention again shown in position in the wearer's eye.

FIG. 5 is a cross section, the plane of which is indicated by the line 5—5 of FIG. 4.

Figure 6:
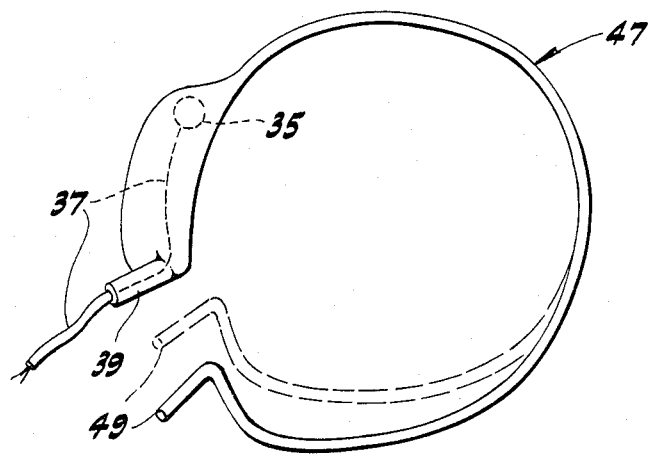
FIG. 6 is an elevational view of the eyelid device carrier of FIGS. 4 and 5 with the carrier shown in full lines in its free position and in dashed lines generally in the position assumed when in the wearer's eye.

The carriers described herein are to retain a sensor or other device for wear by a human having a normal eyeball 11 with the customary somewhat spherical cornea 13 constituting a circular discontinuity by projecting substantially from the general configuration of the adjacent sclera. While geometric lines and terms are used herein, they are not to be taken in a strictly mathematical sense, but rather to convey an approximation of the actual and customary shapes and relationships. The cornea has a size or diameter of a relatively well known amount. The eyeball 11 is situated behind or within a lower eyelid 15 and the upper eyelid 17. The eyelids merge at the medial palpebral commissure 19, near the nose and also merge at the lateral palpebral commissure 21, at the temporal side of the eye. The undersides of the upper eyelid 17 and the lower eyelid 15 are lined with the palpebral conjunctiva 23, which is of particular interest herein.

Pursuant to the invention, there is provided an eyelid device carrier one embodiment of which is shown in FIGS. 1, 2 and 3 carrying the reference numeral 41. This is a structure preferably made of a thermoplastic elastomer or other appropriate material that can be made sterile, is flexible and can be smoothly finished for comfort in use. In this embodiment, the carrier 41 has a partial or split ring with an opening on the nasal side. As can be seen, particularly in FIG. 3, the carrier 41 takes on a relaxed position as shown in solid lines but when held in place in the eye it takes on the position shown in dashed lines, the upward and downward extent being restrained from its resilient opening by means of the superior and inferior fornices of the conjunctiva. Because the split ring of the carrier in conjunction with the use of a flexible material, permits great flexibility and, consequently greater conformability than is possible with prior art carriers, the overall shape of the carrier 41 may, when in place, fit more comfortably within the conjunctival sac.

The split ring shape of the carrier acts as a flexible guide during placement and somewhat regulates location around the cornea thus protecting the cornea itself during placement and removal. Because of the wide variation possible in vertical position of the upper and lower legs 43 and 45, the carrier of FIGS. 1, 2 and 3, can fit an even larger percent of the population with a better quality fit and is more readily retained beneath the eyelids than are the carriers of prior art.

The upper and lower legs 43 and 45, by their inner margins, limit or define an opening 29 of a general elliptical to circular configuration. The opening 29 is especially large and is substantially greater than is the dimension of the normal cornea. That is, there is allowed substantial free space or distance between the circumferential margin 31 of the cornea and the inner surface or margin 27 of the upper and lower legs 43 and 45. Insertion of the carrier 41 under the eyelids is facilitated by its flexible and split nature. The carrier's configuration is such that it can first be inserted into the superior fornix and then utilizing its flexible, split nature, be easily positioned behind the lower eyelid and moved toward the inferior fornix, locating the carrier well away from the cornea 13. Once inserted, the carrier's upper and lower legs 43 and 45 assume a three dimensionally slightly curvilinear configuration within the conjunctival sac.

For the most part, the upper and lower legs 43 and 45 are of relatively small cross-section. Preferably, the cross-sectional diameter of the upper and lower legs 43 and 45 is substantially constant and of the order of about 1 or 2 mm. On the temporal side, the rim forms a widened portion 33 carrying a device 35. The device 35 is disposed in the carrier with a portion exposed at the carrier surface posteriorly or anteriorly, or both so that the device may contact the eye at the sclera, conjunctiva or both. Also, the device carrying portion 33 may be thicker so as to partially encase the sensor or other device, as well as any leads or tubes which may be connected to the device. Typically, the width of portion 33 may be in the range of about 2 mm to 5 mm, and the thickness of the order of 1 mm.

The material from which the carrier 41 is formed should be sufficiently flexible to permit at least some degree of conformation to the shape of the conjunctival sac without exerting pressure against the palpebral conjunctiva or the fornices. At the same time, when placed behind the palpebral conjunctiva, it should be sufficiently rigid to maintain its shape, consistent with its conformal fit beneath the eyelids. To this end it has been found that the material should preferably have a flexural modulus between 2000 kilograms per square centimeter and 10,000 kilograms per square centimeter. Materials which fit these qualifications include thermoplastic elastomers, one example being a polyester sold under the trademark "Hytrel". Other suitable materials include polyurethane and styrene butadiene.

In keeping with its primary purpose, the carrier 41 contains, in the wider portion 33, a sensor or other device 35 of any of several suitable sorts. As can be seen in FIG. 1 the sensor may itself be wider and thicker than the major arc, that is, the narrow portion of the upper and lower legs 43 and 45. The device 35 may be connected to associated indicators, meters, remote sensors and/or comparable equipment through a conductor or other transmission device 37. Toward the exterior of the carrier 41, the transmission device 37 travels through an extension 39. Preferably the extension 39 is integral with the carrier itself and extends in a direction and far enough so as to pass by and project beyond the eyelids, as shown especially in FIG. 1. The extension 39 may serve as a handle for the convenient placement and removal of the carrier.

The flexible, split nature of the carrier facilitates its self-location within the conjunctival sac. The dimensions of the carrier are such that while it is an easy fit in almost all patients of a certain class (e.g. adults or infants), the dimensions and the flexibility of the upper and lower legs 43 and 45, when inserted under the eyelids, cause it to lie in a stable, nonshifting position away from the cornea. The position of the handle or extension 39, which extends outward from between the eyelids, also contributes to preventing the carrier from shifting about after placement. In contradiction to the carriers of the prior art, the present carrier is not usually disturbed by movement of the wearer's eyeball or eyelids. This means in practice that a wearer may tolerate this structure for a much longer time than heretofore and feel less discomfort from its use. That is, the wearer may not only roll his cornea 13 to the left and to the right to a reasonable extent but he may also look upwardly and downwardly from the center with minimal physical contact between the cornea and the upper and lower legs 43 and 45, or with no such contact at all. The presence of the carrier within the eye can be of far less significance to the wearer than heretofore with the prior art. At the same time the device 35 can be maintained more nearly in a stable set position because its carrier is not likely to be shifted or moved by the wearer's eye movement. A more effective, longer lasting employment can be attained.

Due to the flexibility and split nature of the carrier, the carrier itself conforms better to the eye and therefore seats better between the eyeball and the palpebral conjunctiva. Because of this better seating it remains more stable during the time that it is worn. Moreover, the thin cross-section of the carrier, particularly of the upper and lower legs 43 and 45, makes it more comfortable than those of the prior art which are in a closed ring form and are frequently formed of a thicker more rigid material such as polymethylmethacrylate (PMMA). The use of the closed ring carriers in the prior art devices has also been a major cause of their being useful for only about 70% of the population. Because of the wide variation in vertical position of the flexible upper and lower legs 43 and 45, the carrier of FIGS. 1, 2 and 3 can fit an even larger percent of the population and is more readily retained beneath the eyelids than the carriers of the prior art. Futher, the thin cross section, together with the split ring flexibility, substantially eliminates any interference with the physiological parameters being measured.

Referring to FIGS. 4, 5 and 6 still another embodiment of the invention is shown similar to the carrier 41 of FIGS. 1, 2 and 3 in that the ring is not completely closed and is split. In this instance, however, the ring 47 is split on the temporal side. One end of the ring of the carrier 47 terminates in the extension 39 carrying the transmission devices 37 but the other end also terminates in an extension 49 which, as seen particularly in FIG. 4, serves to hook over the lower eyelid 15. The extensions 39 and 49 may together cooperate as a handle for simplification of the placement and removal of the carrier. Again, the shape of the carrier acts as a guide to insertion and somewhat regulates its location around the cornea. Again, as can be seen particularly in FIG. 6 the carrier 47 assumes the position shown in solid lines in its relaxed condition but, when placed in the eye of the wearer assumes the position generally as shown in dashed lines closely within the superior and interior fornices of the conjunctiva.

Figure 7:
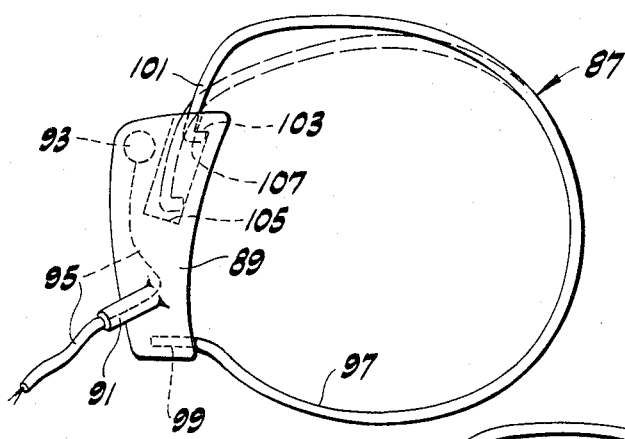
FIG. 7 is an elevational view of still another embodiment of the eyelid device carrier itself showing the carrier in dashed lines generally in the position assumed when located within the wearer's eye and in full lines in its free position outside the wearer's eye.

Referring to FIG. 7 still another embodiment of the invention is shown wherein the carrier 87 takes the form of a one or two piece structure including a generally wide section 89 including an extension 91. The section 89 serves to carry a sensor or other device 93 as well as a conductor or other transmission device 95. The second portion of the carrier 87 incorporates a resilient "wire" of metal or plastic material 97 having one end 99 secured to the section 89. The other end 101 of the wire is held captive by moveably within the section 89 such that it can travel between limits defined by abutments 103 and 105 in the section 89. The end 101 includes an overturned portion 107 which cooperates with the abutment 103 to limit its outward movement. The wire 97 preferably has a biocompatible surface and is formed with sufficient resiliency such that in its most relaxed condition it takes on the position shown in solid lines whereas when it is in place in the eye it takes on a position generally intermediate between the positions shown by the solid and dashed lines. In this intermediate position the outward extent of the wire 97 is, as in the preceding embodiments, limited by the superior and inferior fornices of the conjunctiva such that the end 101 ordinarily lies somewhat intermediate the abutments 103 and 105.

Figure 8:
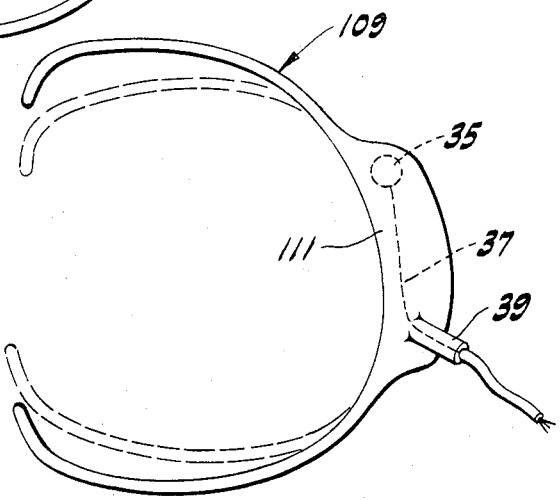
FIG. 8 is an elevational view of another embodiment of the eyelid sensor carrier with the sensor and conductor located on the nasal side.

Still another embodiment of the invention is shown in FIG. 8. The embodiment shown in FIG. 8 is very similar to that shown in FIGS. 1, 2 and 3 with the exception that the wider portion of the carier 109 shown in FIG. 8 is on the nasal side rather than on the temporal side and the spliting of the ring is on the temporal side. Again, the wide portion 111 carries a sensor or other device 35 which may have a transmission device 37 passing through an extension 39 which also lies on the nasal side. In other particulars the carrier 109 of FIG. 8 is like that of FIGS. 1, 2 and 3. With the carrier 109, the conductor 37 extends through the medial palpebral commissure and may be routed along or about the nose of the patient rather than along his temple. Other alternatives, of course, may include a carrier such as shown in FIG. 8 with the conductor extending from the nasal side but with the sensor being positioned in a wider portion of the carrier on the temporal side either above or below the split in the ring. In such instances, of course, the conductor 37 must extend through the extremely narrow rim of the carrier lying against either the superior or inferior fornix. While not specifically shown, the nasal placement, as shown in FIG. 8, could be applied to the other embodiments hereof, as well as to that of FIGS. 1, 2 and 3.

Various general types of detectors might suitably be employed as the device by the described carrier. These include fiber optic sensors and gas sampling devices, as well as chemical, electrical, or electrochemical sensors. In accordance with the type of sensor used, the conductor may be of a nature for transmission of electrical energy, light or like radiation, or gas, and the detecting device may be located remote from the carrier. In addition it should be recognized that the eyelid carrier need not include a conductor coupled to external equipment but may well indeed be a device complete in itself. One such self-contained detector which may be utilized is a sensitized paper or the like. In addition it should be recognized that an electrical detecting device could include an integrated circuit sensor or an electrochemical sensor for the measurement of pH as well as measurement of ions such as of potassium and calcium. Alternatively the device employed with the described carrier could be of therapeutic rather than measuring nature, such as with a drug or other material dispensing device. In this case the conductor may be used to supply additional material to said device. In all forms of the device, it is believed that the undesirable effects of the carrier on the measured physiological parameters of the wearer have been sustantially reduced over the previous practice and that the detecting device is held in position more securely and with less dislodgement than heretofore. Moreover, it is believed that a single size of the carrier as set forth herein is more suitable for a greater portion of the population. In addition, the device has but slight tendency to move within the eye. The more comfortable fit within the wearer's eye will permit its utilization over relatively long periods of time with little or no irritation or discomfort.

What is claimed is:

1. An eyelid device carrier comprising a split, resilient ring having upper and lower legs adapted to be received between the eyeball and the eyelids and defining an opening allowing substantial movement of the eyeball with minimal contact between the cornea and the ring, the vertical distance between said upper and lower legs, with the split resilient ring in relaxed position, being greater than the vertical distance between the inferior and superior conjunctival fornices of the eye whereby the split ends of said ring are adapted to resiliently hold the carrier in position in the eye by being resiliently urged apart and into the conjunctival fornices, at least one device in said ring having a portion exposed for contact with the eye, said ring including a first portion of relatively small cross-section and a second portion of relatively wide cross-section, said device being disposed in said second portion.

2. An eyelid device carrier as defined in claim 1 wherein said ring comprises a flexible material having a flexural modulus of between 2000 kg/cm$^2$ and 10,000 kg/cm$^2$.

3. An eyelid device carrier as defined in claim 2 wherein said device is disposed on the temporal side of said carrier.

4. An eyelid device carrier as defined in claim 1 wherein said ring is split on the nasal side.

5. An eyelid device carrier as defined in claim 4 wherein said device is disposed on the temporal side of said carrier.

6. An eyelid device carrier as defined in claim 1 wherein said ring is split on the temporal side.

7. An eyelid device carrier as defined in claim 6 wherein said device is disposed on the nasal side of said carrier.

8. An eyelid device carrier as defined in claim 6 wherein said device is disposed on the temporal side of said carrier.

9. An eyelid device carrier as defined in claim 1 wherein said device is disposed on the temporal side of said carrier.

10. An eyelid device carrier as defined in claim 1 wherein at least one of the split ends of said ring terminates in a projection from said ring adapted to extend outwardly therefrom beyond the margin of an eyelid.

11. An eyelid device carrier as defined in claim 1 wherein said ring comprises a device carrying portion and a stabilizing portion, said stabilizing portion being formed of resilient wire-like material, one end of said stabilizing portion being attached to said device carrying portion, the other end of said stabilizing portion being moveably retained in said device carrying portion between predetermined limits of movement, said limits defining maximum and minimum opening of said stabilizing portion, said stabilizing portion being resiliently urged toward said maximum opening.

12. An eyelid device carrier as defined in claim 11 wherein said device comprises a sensor.

13. An eyelid device carrier as defined in claim 1 wherein said device comprises a sensor.

* * * * *